US00PP23309P3

(12) United States Plant Patent
Egger

(10) Patent No.: US PP23,309 P3
(45) Date of Patent: Jan. 1, 2013

(54) ***HEUCHERA* PLANT NAMED 'PEACH CRISP'**

(50) Latin Name: ***Heuchera* spp.**
Varietal Denomination: Peach Crisp

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 127 days.

(21) Appl. No.: 13/066,144

(22) Filed: Apr. 6, 2011

(65) Prior Publication Data

US 2012/0260383 P1 Oct. 11, 2012

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant substantially as shown and described, characterized by ruffled leaves, intense rust red spring leaf color, glossy rust red to amber summer leaves, medium plant size, short flowering stalks that are deep red with small white flowers, and excellent vigor.

1 Drawing Sheet

Botanical denomination: *Heuchera* spp.
Variety designation: 'Peach Crisp'.

BACKGROUND OF THE INVENTION

The present invention relates to a new and distinct cultivar of *Heuchera* and given the cultivar name of 'Peach Crisp'. *Heuchera* is in the family Saxifragaceae. *Heuchera* 'Peach Crisp' originated from a planned cross between *Heuchera* 'Café Olé' (U.S. Plant Pat. No. 18,922), as the seed parent, and *Heuchera* 817-1, a proprietary unreleased plant, as the pollen parent. Compared to the seed parent, *Heuchera* 'Café Olé', the new cultivar has rust red foliage rather than brown. Compared to the pollen parent, *Heuchera* 817-1, the new cultivar has leaves that are more ruffled and are rust red rather than purple olive.

Compared to *Heuchera* 'Marmalade' (U.S. Plant Pat. No. 15,945), the new cultivar has a smaller tighter habit, rust red rather than amber leaf color, and shorter flowers.

This new *Heuchera* is distinguished by:

1. ruffled leaves,
2. intense rust red spring leaf color,
3. glossy rust red to amber summer leaves,
4. medium plant size,
5. short flowering stalks that are deep red with small white flowers,
6. and excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two-year-old *Heuchera* 'Peach Crisp' in bloom, growing in a two gallon container in the shade house in late April in Canby, Oreg.

DETAILED PLANT DESCRIPTION

The following is a detailed description of the new *Heuchera* cultivar based on observations of two-year-old specimens grown in two gallon containers outdoors in full sun in April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Basal rosette, herbaceous perennial.
*Hardiness*.—USDA Zone 4 to 9.
*Size*.—22 cm tall from top of the foliage to the ground and 47 cm wide.
*Habit*.—Mounding.
*Vigor*.—Excellent.
*Roots*.—Fibrous, freely branching, fine, and white in color; roots develop easily from cuttings.

Leaf:

*Type*.—Simple.
*Arrangement*.—Basal.
*Shape*.—Ovate.
*Lobing/division*.—5 main lobes, with 2 to 3 shallow secondary lobes.
*Venation*.—Palmate.
*Margins*.—Crenate and undulate.
*Apex*.—Mucronulate.
*Base*.—Cordate, lobes overlapping at the base.
*Blade size*.—Grows to 7.5 cm long and 6 cm wide.
*Surface texture*.—Both sides glandular.
*Petiole description*.—Grows to 18 cm long and 2 mm wide, glandular hairs, Greyed Purple 186A.

*Leaf color*.—Spring, topside new mature leaves, between Greyed Purple 185A and 187C lightening to Greyed Orange 174D tinted Greyed Purple 184D, bottom side Greyed Purple 187B; summer and fall topside Greyed Orange 177A and 176A, bottomside Greyed Purple 187B.

Inflorescence:

*Size*.—Grows to 4.4 cm wide and 19 cm long.

*Type*.—Thyrse.

*Number of flowers per thyrse*.—80 to 120 per thyrse.

*Number of thyrse*.—About 13 in first spring bloom.

*Peduncle*.—Grows to 42 cm tall, 3 mm to 4 mm wide at base, Greyed Purple 187A, glandular hairs, with 2 to 4 petiolate leaves (ovate, blades grow to 4 cm long and 4 cm wide, 5 lobed, margin undulate, and crenate, color the same as the leaves).

*Pedicel*.—Variable in size, with glandular hairs, Greyed Purple 187A.

*Bloom period*.—Late April to June in Canby, Oreg.

Flower bud:

*Size*.—2.5 mm wide and 4 mm long.

*Description*.—Glandular puberulent, ovoid.

*Color*.—Top ⅔ Red Purple 62D, bottom ⅓ Red Purple 58A.

Flower:

*Type*.—Perfect.

*Shape*.—Campanulate.

*Size*.—5 mm long and 3 mm wide.

*Petal description*.—5 in number, 2 mm long, spatulate with a clawed base, reflexed, tip acute, margin entire, glabrous on top and bottom side, White NN155C on both sides.

*Calyx description*.—5 mm long and 3 mm wide, with 5 lobes, divided ½ way to the base, glandular hairs on both sides, tip obtuse, margin entire, both sides White N155C on top ⅔, Red Purple 58D on bottom ⅓.

*Stamen description*.—5 in number, 2.5 mm long, filament 2 mm long, White NN155B, anthers White 155A, no pollen, male sterile.

*Pistil description*.—One central two beaked pistil, 4 mm long, ovary 2 mm long and Yellow Green 145B, style 2 mm long, White NN155B.

*Fragrance*.—None.

*Lastingness*.—Each thyrse blooms for about 2 weeks on the plant.

Fruit:

*Type*.—Two beaked capsule.

*Size*.—7 mm deep by 2 mm wide.

*Fertility*.—Good.

*Color*.—Greyed Brown 199A.

Seed:

*Shape*.—Linear.

*Size*.—2 mm long.

*Color*.—Black, RHS 202A.

Disease and pest tolerance: No known resistance to rust, a common problem with light leaf type *Heuchera*. Excellent disease tolerance to powdery mildew. All *Heuchera* are susceptible to root weevils.

I claim:

1. A new and distinct *Heuchera* plant as herein illustrated and described.

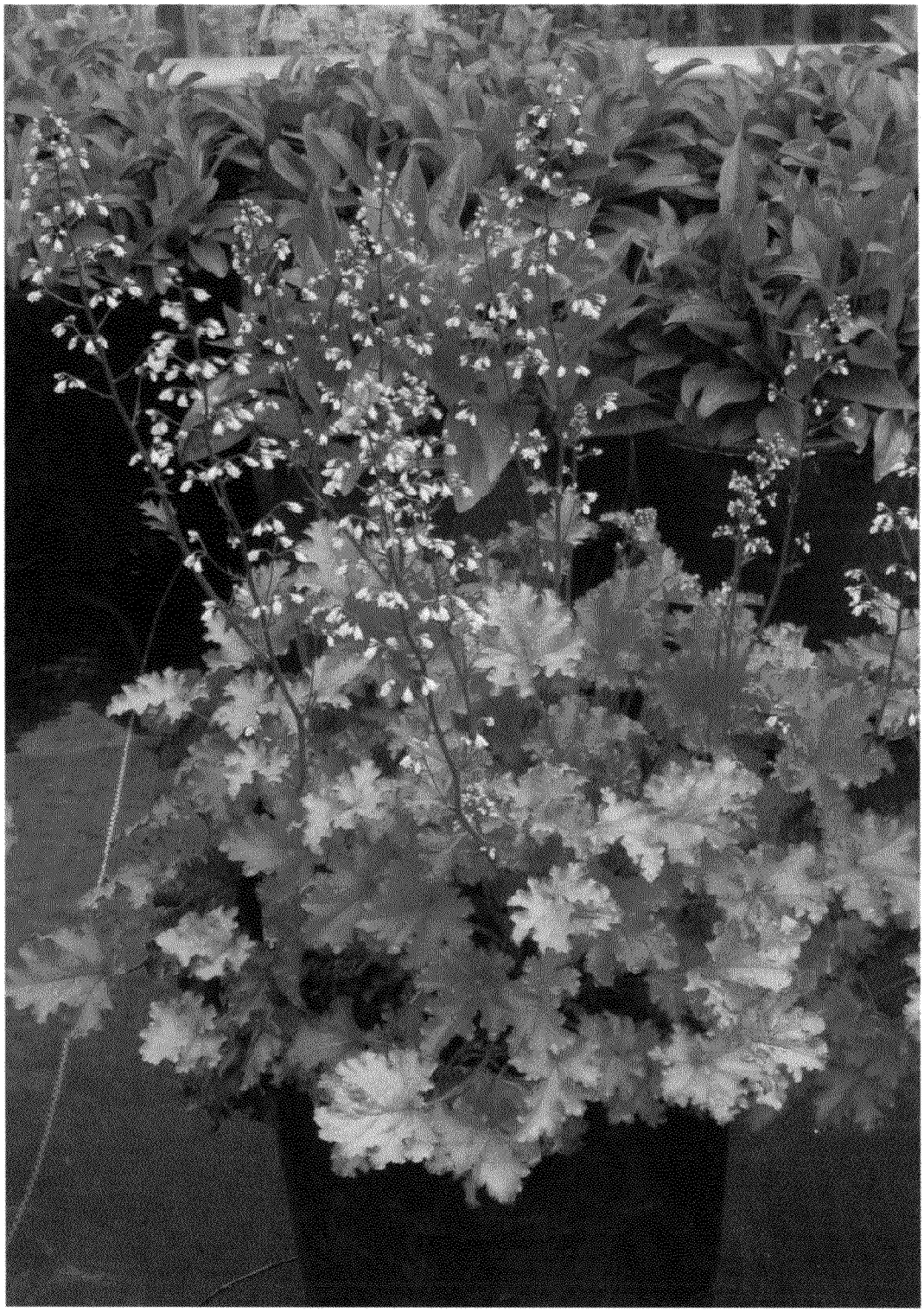

* * * * *